(12) United States Patent
Benson

(10) Patent No.: US 8,674,056 B2
(45) Date of Patent: Mar. 18, 2014

(54) METHODS FOR PRODUCING LACTIDE WITH RECYCLE OF MESO-LACTIDE

(75) Inventor: Richard Douglas Benson, Long Lake, MN (US)

(73) Assignee: NatureWorks LLC, Minnetonka, MN (US)

( * ) Notice: Subject to any disclaimer, the term of this patent is extended or adjusted under 35 U.S.C. 154(b) by 43 days.

(21) Appl. No.: 13/203,211

(22) PCT Filed: Mar. 12, 2010

(86) PCT No.: PCT/US2010/027119
§ 371 (c)(1),
(2), (4) Date: Aug. 24, 2011

(87) PCT Pub. No.: WO2010/105143
PCT Pub. Date: Sep. 16, 2010

(65) Prior Publication Data
US 2011/0306749 A1 Dec. 15, 2011

Related U.S. Application Data

(60) Provisional application No. 61/159,938, filed on Mar. 13, 2009.

(51) Int. Cl.
*C08G 63/08* (2006.01)
(52) U.S. Cl.
USPC ............... 528/347; 525/415; 526/67; 526/68; 549/274
(58) Field of Classification Search
USPC ........ 525/415; 526/67, 68; 528/357; 549/274
See application file for complete search history.

(56) References Cited

U.S. PATENT DOCUMENTS

| 5,247,058 A | 9/1993 | Gruber |
| 5,258,488 A | 11/1993 | Gruber |
| 5,338,822 A | 8/1994 | Gruber et al. |
| 5,357,035 A | 10/1994 | Gruber |
| 5,536,807 A | 7/1996 | Gruber |
| 5,700,435 A | 12/1997 | Bischof |
| 6,005,067 A | 12/1999 | Gruber |
| 6,277,951 B1 | 8/2001 | Gruber |
| 6,310,218 B1 | 10/2001 | O'Brien |
| 6,326,458 B1 | 12/2001 | Gruber |
| 2006/0014975 A1* | 1/2006 | Coszach et al. ............... 560/179 |

FOREIGN PATENT DOCUMENTS

WO 95/09879 A 4/1995

OTHER PUBLICATIONS

Tsukegi et al, "Racemization behavior of L-L-lactide during heating", Polymer Degradation and Stability 92 (2007) 552-559.
Nomura et al., "Stereoselective Ring-opening polymerization of a racemic lactide . . . ", Chem. Eur J. 2007, 13, 4433-4451.

* cited by examiner

*Primary Examiner* — Gregory Listvoyb
(74) *Attorney, Agent, or Firm* — Gary C Cohn PLLC

(57) ABSTRACT

An S,S- and R,R-lactide stream suitable for polymerization is prepared by producing a low molecular weight poly(lactic acid), depolymerizing the low molecular weight poly(lactic acid) to form a mixture of S,S-, R,R- and meso-lactide, and separating meso-lactide from this mixture to form an S,S- and R,R-lactide stream. Meso-lactide is recycled into the process, and shifts the mole fractions of the lactides in the lactide mixture that is produced.

41 Claims, 1 Drawing Sheet

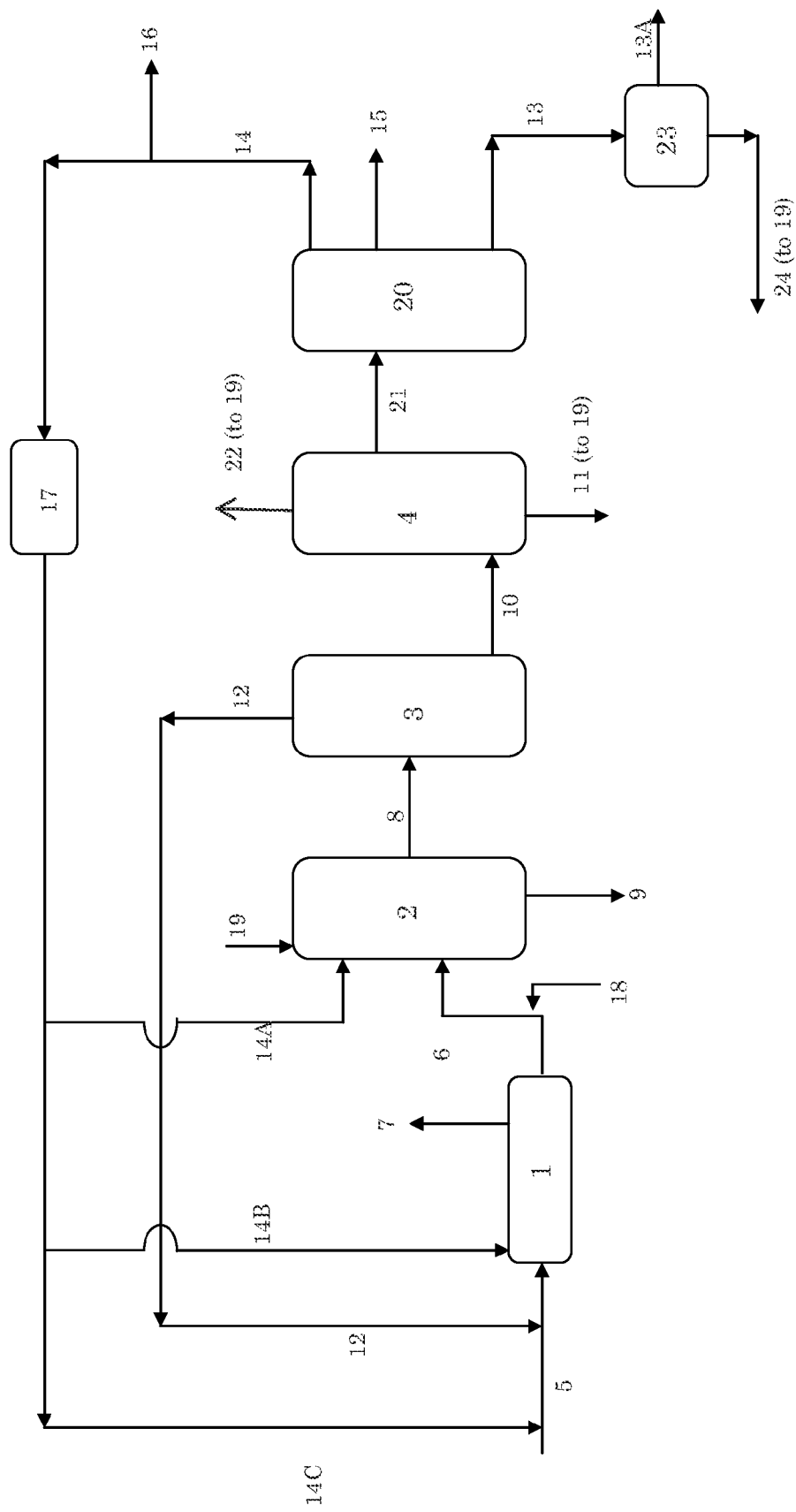

METHODS FOR PRODUCING LACTIDE WITH RECYCLE OF MESO-LACTIDE

This application claims benefit of U.S. Provisional Patent Application No. 61/159,938, filed 13 Mar. 2009.

This invention relates to methods for making lactide and polylactide (PLA).

Polylactide resins are made industrially by converting lactic acid to lactide, which is then polymerized. Lactic acid is a molecule with one chiral center, and so it exists in two enantiomeric forms, the so-called R-(or D-) enantiomer and the S-(or L-) enantiomer. Two molecules of lactic acid can condense, with the elimination of two molecules of water, to form a 3,6-dimethyl-1,4-dioxane-2,5-dione, which is commonly referred to as "lactide". Lactide can be considered as being made up of two "lactic units", each of which has the structure:

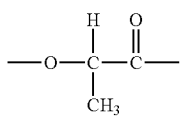

Each lactic unit in a lactide molecule contains one chiral center and exists in either the R- or the S-form. A lactide molecule can take one of three forms: 3S,6S-3,6-dimethyl-1,4-dioxane-2,5-dione (S,S-lactide), 3R,6R-3,6-dimethyl-1,4-dioxane-2,5-dione (R,R-lactide), and 3R,6S-dimethyl-1,4-dioxane-2,5-dione (R,S-lactide or meso-lactide). These have the following structures:

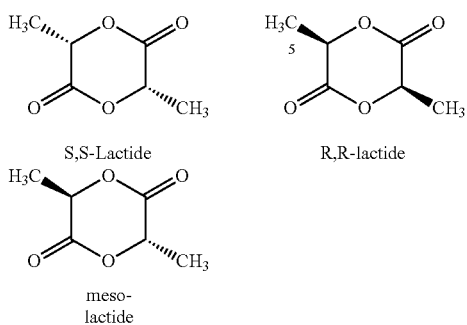

S,S-lactide and R,R-lactide are a pair of enantiomers, while meso-lactide is a stereoisomer.

Polylactide is formed by polymerizing lactide. Polylactide, like lactide, is made up of lactic units. When an S,S-lactide molecule is incorporated into the polylactide polymer chain, it adds two adjacent S-lactic units. R,R-lactide brings in two adjacent R-lactic units, and meso-lactide brings in one S-lactic unit and an adjacent R-lactic unit.

The ratio and distribution of the R- and S-lactic units in the polylactide impact its crystalline behavior and physical properties. When neither the R-lactic units nor the S-lactic units are greatly in excess, the polylactide is an amorphous material that can crystallize slowly if at all. When one type of lactic unit is more predominant, the polylactide resin can become semi-crystalline. A semi-crystalline material is usually formed when the ratio of the two enantiomeric forms exceeds about 90:10. As the enantiomer ratio increases from 85:15 towards 100:0, the polylactide tends to become more crystalline in character, i.e., crystallizes more easily and is capable of developing a greater amount of crystallinity. It is not important whether it is the R- or S-form that is predominant. However, S-lactic units usually predominate, because most industrial processes produce lactic acid in fermentation processes, and most microorganisms that are used in fermentation processes produce the S-enantiomer.

Thus, commercial polylactide product grades are often distinguished from each other by the relative proportions of R-lactic units and S-lactic units they contain. Polylactides in which one form is very highly predominant are typically used in applications in which a highly crystalline material is needed (typically for its thermal properties), or in which, due to processing constraints, it is important that the product develop its crystallinity rapidly. In those cases, the predominant form of lactic acid, either the R- or the S-form, usually will constitute at least 98% of the lactic units in the polymer. Polylactides containing the two forms of lactic units in a ratio of from 85:15 to 98:2 are used in applications in which only a moderate amount of crystallinity is needed, or in which a slower rate of crystallization is acceptable. Polylactides containing no more than 85% of either form of lactic units tend to be mainly amorphous materials, which develop only small amounts of crystallinity at most and tend to do so slowly if at all.

It is therefore very important to control the ratio of the R- and S-forms of lactic units in a polylactide manufacturing process.

Processes that are suitable for large-scale production of polymer grade lactide from lactic acid are described, for example, in U.S. Pat. Nos. 5,247,058, 5,258,488, 5,357,035, 5,338,822, 6,005,067, 6,277,951 and 6,326,458. The processes described in these patents generally involve forming a low molecular weight poly(lactic acid), and then depolymerizing the low molecular weight poly(lactic acid). The depolymerization step produces lactide. The lactide is then purified to separate it from water, residual lactic acid, linear lactic acid oligomers and other impurities as may be present. This can be done by distillation or by other methods such as recrystallization, either from a solvent or from a melt.

The starting lactic acid is usually of very high optical purity. However, the starting material is subjected to elevated temperatures as it is converted to the low molecular weight poly(lactic acid) polymer and subsequently depolymerized. Some racemization (i.e., conversion of one enantiomeric form to the other) occurs under those conditions. In addition, a much smaller amount of racemization may occur as the lactide is purified. Perhaps 1 to 10% of the lactic units in the starting material may become racemized in this fashion to form the other enantiomer, although this amount can vary quite substantially in any given manufacturing process. Because this racemization occurs, the lactide obtained from the process will be a mixture of S,S-lactide, R,R-lactide and meso-lactide.

In most commercial-scale processes, the starting material is in the S-enantiomeric form, so that the net effect of racemization is to convert some of the S-lactic units to R-lactic units. In that case, the predominant form of the lactide product will be S,S-lactide. The next most common form will be meso-lactide, as each of the R-lactic units is most likely to become paired with an S-lactic unit rather than another R-lactic unit. Some "R,R-lactide" can be formed from two R-lactic acid units, but the amount of R,R-lactide that is formed is typically very small due to the small concentration of R-lactic units in the system.

When such a lactide mixture is polymerized, the ratio of S- and R-lactic units in the resulting polymer is determined almost entirely by the amount of meso-lactide in the mixture. The ratio of S- to R-lactic units plays a large role in the crystalline properties of the polylactide, and it is therefore important to control this ratio in the lactide stream that is taken to polymerization.

It is often the case that the lactide mixture produced as described above contains more meso-lactide (and therefore more R-lactic units) than is wanted in the downstream polymerization step. In such a case, some or all of the meso-lactide must be removed from the lactide mixture. The remaining stream is depleted in meso-lactide, relative to the starting lactide mixture. The optical purity of the remaining lactide, and that of the polylactide made from it, is therefore mainly controlled by the extent to which meso-lactide has been removed. If very high optical purity is needed, all or nearly all of the meso-lactide may be removed from the lactide stream that is taken to polymerization. It is more typical to leave some meso-lactide in the stream, especially when semi-crystalline polylactide grades are to be produced.

A couple of methods are available by which meso-lactide can be separated from S,S-(or R,R-) lactide. As mentioned in U.S. Pat. No. 6,326,458, meso-lactide is more volatile than S,S- and R,R-lactide and so can be separated from S,S- and R,R-lactide by a fractional distillation. It is also possible to remove meso-lactide from S,S- and R,R-lactide by melt crystallization methods, as described in U.S. Pat. Nos. 4,883,745, 4,983,747, 5,463,086 and 6,310,219. Solvent recrystallization is another useful method.

In principle at least, meso-lactide that is removed from the lactide mixture can be stockpiled and added back into a predominately S,S-lactide (or predominantly R,R-) stream, if it is desired at some later time to produce a more amorphous polylactide grade that has a higher proportion of the R-enantiomer (or S-enantiomer as the case may be). However, in practice, this meso-lactide stream may be highly contaminated with impurities. During the separation of the meso-lactide, the impurities tend to become more concentrated in the meso-lactide stream and less concentrated in the remaining lactide. This is beneficial because the lactide stream that is taken to polymerization is cleaner. But the higher impurity level in the meso-lactide stream tends to make that stream unsuitable for polymerization. In actual practice, the difficulty and cost of removing the impurities from the meso-lactide has been such that the meso-lactide is usually discarded or used in other, lower-value applications. This reduces overall yields and increases the overall cost of the process.

A subset of these impurities is sometimes referred to herein as intermediate-boiling impurities. The intermediate-boiling impurities have volatilities very close to those of S,S-lactide and meso-lactide, and therefore are difficult to remove, especially via distillation methods. The intermediate-boiling impurities can be characterized by their relative volatility in a lactide matrix at a given set of distillation conditions; they tend to have relative volatilities of from 1.001 to 1.5 relative to S,S-lactide when distilled from a lactide matrix. The intermediate-boiling impurities typically have boiling points in the range from slightly below that of meso-lactide to slightly above that of S,S-lactide, i.e. from about 155 to about 180° C. at 50 Torr pressure.

A significant quantity of impurities still are present in the lactide stream that remains after meso-lactide is removed, because the relative masses of the streams (the meso-lactide stream being generally of much smaller volume), and because in most cases meso-lactide is not separated completely. Generally speaking, the more meso-lactide that remains, the more impurities, especially troublesome intermediate-boiling impurities, will remain in the stream that is taken to polymerization. This can cause problems when the lactide stream is polymerized, such as slower polymerization rates. An additional purification step may be required before or after the polymerization is performed.

Therefore, it would be desirable to reduce these yield losses and provide a more efficient method for producing a polymerizable lactide stream. It would also be desirable to provide an effective method of producing a highly purified lactide stream which is useful for preparing semi-crystalline grades of polylactide.

This invention is a process for producing a polymerizable lactide stream, comprising:

a) forming a low molecular weight poly(lactic acid);

b) depolymerizing the low molecular weight poly(lactic acid) to form a crude lactide that includes meso-lactide, S,S-lactide and R,R-lactide, wherein either S,S-lactide or R,R-lactide is the non-predominant lactide;

c) separating meso-lactide from the crude lactide in one or more steps such that 1) a meso-lactide-enriched stream is formed in which the mole fraction of meso-lactide is at least 0.8; and 2) a purified S,S- and R,R-lactide stream is formed; and d) recycling at least a portion of the meso-lactide stream directly or indirectly back into step a) or step b), whereby at least a portion of the meso-lactide in the recycled meso-lactide stream is converted to a mixture of S,S-, meso- and R,R-lactide and the mole fraction of the non-predominant lactide (as described below) in the crude lactide produced in step b) is increased relative to when step d) is not performed.

The mole fraction of the non-predominant lactide in the crude lactide may increase, due to the recycling of the meso-lactide, by 0.002 (i.e., by 0.2%) or more. Typically, that mole fraction will increase by 0.005 to 0.1 (by 0.5 to 10%), by 0.005 to 0.05 (by 0.5 to 5%), or by 0.005 to 0.03 (i.e., by 0.5 to 3%).

The enantiomeric form of lactic unit (either S- or R-) that is present in the higher mole fraction in the process is referred to herein as the "predominant" lactic acid unit or "predominant" enantiomer. Conversely, the lactic unit that is present in the lower mole fraction in the process is referred to herein as the "non-predominant" or "less predominant" lactic unit or "non-predominant" or "less predominant" enantiomer. In the case of lactide, the "predominant" lactide is either S,S- or R,R-lactide in each case, depending on which one is present in the greater mole fraction. The one which is present in the smaller mole fraction is, correspondingly, the "non-predominant" or "less predominant" lactide. Meso-lactide is neither the "predominant" or "non-predominant" lactide form, regardless of its mole fraction. Mole fractions are in each case the number of moles of the lactic unit or lactide under consideration, divided by the total number or moles of lactic units or lactide, respectively, in the system as a whole or in a particular process stream, as indicated by the context.

One effect of recycling the meso-lactide stream is that the mole fractions of S,S-lactide, meso-lactide and R,R-lactide will change in the crude lactide stream. The mole fraction of meso-lactide in the crude lactide will be increased. When the S-enantiomer is the predominant enantiomer in the system, then the mole fraction of R,R-lactide will be increased, with the increase in R,R-lactide and meso-lactide being at the expense of a lower mole fraction of S,S-lactide. When it is instead the R-enantiomer that is predominant, then the mole fraction of S,S-lactide in the crude lactide will be increased, with the increase in S,S-lactide and meso-lactide coming at the expense of a lower mole fraction of R,R-lactide.

Surprisingly, it has been found that this change in mole fractions among the various forms of lactide, in particular the increase in the mole fraction of the non-predominant component (S,S- or R,R-lactide) can not only be tolerated, but it can in fact provide significant benefits to the process.

Another benefit of the inventive process is that less meso-lactide is needed in the S,S- and R,R-lactide stream that is taken to polymerization, to produce a given grade of polylactide. More of the non-predominant lactic units necessary to produce a specific grade of polylactide polymer are instead supplied by the non-predominant lactide (either S,S-lactide or R,R-lactide). Because less meso-lactide is needed, one can more completely separate the meso-lactide from the S,S- and R,R-lactide stream. Because the separation is more complete, a greater proportion of impurities, particularly the intermediate-boiling impurities, are removed with the meso-lactide. The result is a cleaner S,S- and R,R-lactide stream. Therefore, this process can produce a cleaner S,S- and R,R-lactide stream, at a given ratio of S- to R-lactic units in the stream, than in an otherwise like process that excludes the meso-lactide recycle step. The cleaner S,S- and R,R-lactide stream often polymerizes at faster rates.

Because a lower level of these impurities can be obtained (at a given proportion of less predominant lactic units in the stream), one can reduce or even eliminate the capital and/or operating costs associated with removing those impurities from the S,S- and R,R-lactide stream before it is polymerized, or from the polymer after it is polymerized.

The amount of meso-lactide that is recycled will have a direct impact on the mole fractions of S,S- and R,R-lactide produced by the system. The more meso-lactide that is recycled, the more of the non-predominant lactide will be produced. By adjusting the amount of meso-lactide that is recycled (relative to other process streams), the relative amounts of S,S-lactide and R,R-lactide that are produced can be varied to a predetermined value.

Because the composition of the lactide stream that is polymerized is changed due to the meso-lactide recycle, the composition of the polylactide that is produced from it also changes. As described in U.S. Pat. No. 5,536,807, each meso-lactide molecule polymerizes to form an R,S dyad, i.e., an S-lactic unit adjacent to an R-lactic unit. S,S-lactide and R,R-lactide, on the other hand, polymerize to form S,S- and R,R-dyads, respectively. For example, the copolymerization of S,S-lactide with meso-lactide (S,S-lactide being predominant) results in a polymer in which strings of adjacent S-lactic units are interrupted mainly by single R-lactic units. On the other hand, S,S-lactide and R,R-lactide copolymerize to form a polylactide which mainly contains strings of adjacent S-lactic units interrupted mainly by two R-lactic units, rather than single R-lactic units (again, assuming that S,S-lactide is predominant). As discussed in U.S. Pat. No. 5,536,807, a copolymer of X moles of S,S-lactide and Y moles of R,R-lactide (X being much larger than Y) will tend to have crystalline properties similar to that of a copolymer of X moles of S,S-lactide and Y moles of meso-lactide, even though the S,S-lactide/R,R-lactide copolymer will have twice as many R-lactic units in the polymer chain. This phenomenon is understood as being due to the average length of the sequences of consecutive S-lactic units in the polymer, which is statistically very close to the same in the two cases. The length of R-lactic sequences has little bearing on the crystallinity, as long as their average length is small in relation to the average length of the S-lactic units. An analogous situation exists in copolymers of S,S- and R,R-lactide when Y is much larger than X. In that case, the polylactide will contain mainly strings of R-lactic units that are interrupted by S,S-dyads.

The invention, therefore, allows the process to operate at significantly higher levels of the less predominant form of lactic units (typically the R-enantiomer) while still producing a polylactide having equivalent crystalline properties. It also makes the process less sensitive to small changes in the ratio of the S- and R-enantiomers.

The general process for producing lactide by forming a low molecular weight poly(lactic acid), followed by depolymerizing the low molecular weight poly(lactic acid) to form lactide is well-known and described, for example, in U.S. Pat. Nos. 5,247,058, 5,258,488, 5,536,807, 5,357,035, 5,338,822, 6,005,067, 6,277,951, 6,310,218 and 6,326,458 and WO95/09879. Except for the recycling of the meso-lactide stream as described herein, the processes described in those and similar references can be conducted, with regard to this invention, in the general manner described in those references, and those process steps will be described only briefly below.

The low molecular weight poly(lactic acid) is a polymer of lactic acid units, suitably prepared by forming a concentrated lactic acid or lactic acid derivative stream that contains from 60 to 95% by weight lactic acid or lactic acid derivative in water or, less preferably, another solvent. The lactic acid derivative may be, for example, a lactic acid ester, a lactic acid salt, a lactic acid oligomer, and the like. The starting lactic acid or lactic acid derivative should contain at least 90%, preferably at least 95%, more preferably at least 98% and still more preferably at least 99% of either the S- or R-enantiomer, and no more than 10%, preferably no more than 5%, more preferably no more than 2% and even more preferably no more than 1% of the other enantiomer. This stream may contain some oligomeric species that form as the lactic acid or derivative is concentrated. The stream is then further concentrated by removing water (or a lower alcohol in the case of a lactic acid ester) and solvent (if any) in an evaporator. This causes the lactic acid or lactic acid derivative to condense, eliminating water or a lower alcohol as the condensation by-product. As this is an equilibrium reaction, the removal of condensation products favors the further condensation of the lactic acid or derivative. A low molecular weight poly(lactic acid) formed this way has a number average molecular weight of up to about 5000, preferably from 400 to 3000. The low molecular weight poly(lactic acid) may also include non-lactic chemical species which are sometimes added to control molecular weight or improve specific processing properties.

The low molecular weight poly(lactic acid) is then depolymerized by subjecting it to an elevated temperature and subatmospheric pressures, typically in the presence of a depolymerization catalyst. Conditions are generally selected to (1) minimize residence time, as doing so reduces the amount of racemization that can occur, and (2) vaporize the crude lactide that is formed. Like the polymerization reaction, the depolymerization is an equilibrium reaction. Removal of the lactide as it is formed favors the production of additional lactide. Therefore, continuous removal of crude lactide is preferred. One or more stabilizers can be present during this step as described in WO 95/09879.

The crude lactide formed in the depolymerization step contains a mixture of S,S-lactide, meso-lactide and R,R-lactide. It often contains various types of impurities, such as residual water, some lactic acid (or alcohol and ester, if esters are used as the starting material), some linear oligomers of lactic acid, and usually some other reaction by-products, which include some intermediate-boiling impurities as described before. Meso-lactide is separated from the crude lactide. This can be done by methods such as melt crystallization, but a preferred method is to fractionally distill the crude lactide stream in one or more steps.

The crude lactide may undergo one or more purification steps prior to or simultaneously with this separation. For example, the lactide may be partially condensed to separate it from more volatile impurities. Alternatively, the crude lactide can be purified by melt crystallization methods as described in U.S. Pat. No. 6,310,218, or by solvent crystallization methods. A third approach is to distill off some or all of the impurities that are significantly more volatile than meso-lactide, such as water, residual lactic acid or lactic ester starting materials, and other small organic compounds. Such a distillation step can be performed prior to or simultaneously with a fractional distillation step(s) in which meso-lactide is separated from S,S- and R,R-lactide. It is generally preferred to remove most of the more volatile impurities at least from the crude lactide before separating out meso-lactide.

The separation step or steps are conducted under conditions sufficient to produce at least one meso-lactide enriched stream and at least one purified S,S- and R,R-lactide stream. The purified S,S- and R,R-lactide stream contains the bulk of the S,S- and R,R-lactide that were present in the crude lactide. If a distillation approach is used, other process streams may be taken from the distillation step or steps. These may include a lights stream (if those materials are not removed beforehand), and a bottoms stream, which contains materials that are less volatile than S,S- or R,R-lactide, as well as one or more additional impurity streams.

The process may be operated such that the meso-lactide is not completely separated out, in which case the purified S,S- and R,R-lactide stream will contain some meso-lactide. However, the purified S,S- and R,R-lactide stream is in each case depleted in meso-lactide relative to the meso-lactide stream, meaning that the mole fraction of meso-lactide in the purified S,S- and R,R-lactide stream is lower than in the meso-lactide stream and than in the crude lactide.

In addition, the S,S- and R,R-lactide stream is depleted of impurities, preferably including "intermediate-boiling" impurities as described before. "Depletion" in this case is with reference to the crude lactide stream immediately prior to the separation of the meso-lactide; the weight ratio of these impurities to the lactide content of the S,S- and R,R-lactide stream is lower than the weight ratio of the impurities to the lactide content of the crude lactide stream. This relationship can be expressed by the inequality $$1 > \frac{I_{SR}/(I_{SR} + L_{SR})}{I_{crude}/(I_{crude} + L_{crude})} \quad \text{(Equation 1)}$$

where $I_{SR}$ represents the weight of the impurities in the S,S- and R,R-lactide stream, $L_{SR}$ represents the weight of lactide in the S,S- and R,R-lactide stream, $I_{crude}$ represents the weight of the impurities in the crude lactide stream immediately prior to the separation of the meso-lactide and $L_{crude}$ represents the weight of lactide in the crude lactide stream immediately prior to the separation of the meso-lactide. Preferably, the ratio in equation 1 is less than 0.1, more preferably less than 0.05 and even more preferably less than 0.01. An advantage of the invention is that an S,S- and R,R-lactide stream can be produced that has very low levels of the impurities.

The impurity level in the purified S,S- and R,R-lactide stream is affected by how completely the meso-lactide is separated from the S,S- and R,R-lactide stream. Many impurities tend to partition disproportionately towards the meso-lactide stream, although some amount typically will remain with the purified S,S- and R,R-lactide stream. The more completely the meso-lactide is separated from the purified S,S- and R,R-lactide stream, the lower the content of impurities in the purified S,S- and R,R-lactide stream will be. Accordingly, it is preferred to reduce the level of meso-lactide in the purified S,S- and R,R-lactide stream as much as possible, consistent with the necessary enantiomeric composition of the stream that goes forward to be polymerized, to reduce the level of impurities in that stream.

Preferably, the separation is conducted under conditions which produce a purified S,S- and R,R-lactide stream that contains a mole fraction of 0.05 or less of meso-lactide (i.e., no more than about 5% by weight meso-lactide). The S,S- and R,R-lactide stream more preferably contains a mole fraction of 0.02 or less, even more preferably of 0.01 or less, of meso-lactide. The S,S- and R,R-lactide stream may, for example, contain a mole fraction of from 0 to 0.01, from 0 to 0.005 or from 0 to 0.003 of meso-lactide.

All mole fractions described herein are based on the total moles of lactide in the stream under discussion.

The meso-lactide stream contains mainly meso-lactide. The meso-lactide stream typically contains at least 60% by weight of meso-lactide, and may contain at least 80% or at least 90% by weight of meso-lactide, based on the total weight of the stream. It may contain small quantities of S,S- or R,R-lactide, but these together generally constitute no more than about 15%, preferably no more than 10% and even more preferably no more than 5% by weight of the lactide content of the stream. The mole fraction of the meso-lactide (relative to all lactide species) in this stream should be at least 0.80. Thus, the meso-lactide stream is enriched in meso-lactide, compared with the S,S- and R,R-lactide stream and compared with the crude lactide stream.

Intermediate-boiling and other impurities tend to become concentrated in the meso-lactide stream when the meso-lactide is separated from the crude lactide stream, and so the meso-lactide stream becomes enriched in those impurities, relative to the crude lactide stream just prior to the separation, as expressed by the inequality $$1 < \frac{I_{meso}/(I_{meso} + L_{meso})}{I_{crude}/(I_{crude} + L_{crude})} \quad \text{(Equation 2)}$$

where $I_{meso}$ represents the weight of the impurities in the meso-lactide stream, $L_{meso}$ represents the weight of lactide in the meso-lactide stream, and $I_{crude}$ and $L_{crude}$ are as defined with respect to equation 1.

At least a portion of the meso-lactide stream is recycled directly or indirectly into step a) or step b) of the process, as described more fully below.

FIG. 1 is a schematic diagram illustrating an embodiment of the process of the invention. The embodiment illustrated in FIG. 1 illustrates various preferred or optional features. FIG. 1 is not intended to show specific engineering features or details, including the design of the various components shown. In addition, auxiliary equipment such as various valves, pumps, heating and cooling equipment, analytical, control devices and the like are not shown, but of course can be used as necessary or desirable.

In FIG. 1, lactic acid or lactic acid derivative stream 5 containing water or, less preferably, another solvent, is fed into prepolymer reactor 1. The lactic acid or lactic acid derivative concentration in feed stream such as stream 5 preferably is at least 60% by weight, and may be as high as 95% by weight, preferably as high as 90% by weight. Lactic acid may be obtained from a fermentation broth, which is preferably concentrated to within the aforementioned ranges in an upstream process step which is not shown in FIG. 1. The starting material is heated in prepolymer reactor 1 to cause the lactic acid or lactic acid ester to condense to form a low molecular weight poly(lactic acid) as described before. Most of the water and solvent (if any) are removed from prepolymer reactor 1 as stream 7. In addition, the condensation byproducts that are formed in the polymerization reaction (water in the case of lactic acid, a lower alcohol in the case of a lactic acid ester) are also mainly removed as part of stream 7. Stream 7 can be discarded, or all or any portion of it can be recycled to an earlier stage in the process, or into an upstream fermentation process for producing lactic acid or lactic acid derivative. Any recycled portion of stream 7 can be purified before being recycled, and if desired part of stream 7 can be taken as a purge stream to remove impurities from the process.

Prepolymer reactor 1 is essentially a reactor and evaporator, which can be of any convenient design. As with all other process steps in which the lactic acid and its derivatives are exposed to elevated temperatures, racemization can occur in prepolymer reactor 1. Racemization is random, as S-lactic acid can racemize to R-lactic acid and vice versa. However, because one enantiomer is predominant, the net effect of racemization is that the concentration of the non-predominant enantiomer increases at the expense of the predominant enantiomer, and optical purity is reduced. Although some racemization can be tolerated in this process, it is generally preferred to employ conditions that minimize racemization in the prepolymer reactor, as well as in every other process step that involves exposure of the lactic acid and downstream reaction products to elevated temperatures. In most cases, these conditions include minimizing of the amount of time at which the materials are exposed to those elevated temperatures. Accordingly, the prepolymer reactor and other equipment are preferably designed to provide short contact times and to minimize process temperatures, such as through the use of subatmospheric pressures to reduce needed operating temperatures.

Low molecular weight poly(lactic acid) stream 6 is removed from prepolymer reactor 1 and transferred to lactide reactor 2, where it is depolymerized to form lactide. Lactide reactor 2 is again essentially an evaporator, and can be of many types as described in WO95/09879. Examples of suitable lactide reactors include, for example, forced circulation, short path or short tube, long-tube vertical, long-tube horizontal, falling film, agitated thin-film and disk evaporators. Film-generating evaporators, especially falling film and agitated falling film evaporators as described in WO 95/9879, are especially preferred. Various types of staged reactors are also suitable. Lactide reactor 2 is preferably operated at a pressure of from about 1 to about 100 mm Hg, more preferably from about 2 to about 60 mm Hg. An elevated temperature, preferably from about 180 to 300° C. and more preferably from 180 to 250° C., is used.

The depolymerization reaction that occurs in lactide reactor 2 is usually catalyzed. In the embodiment shown, catalyst is introduced to prepolymer stream 6 upstream of lactide reactor 2, through catalyst stream 18. It is also possible to introduce catalyst stream 18 directly into lactide reactor 2.

Crude lactide and a bottoms mixture are formed in lactide reactor 2. The bottoms mainly include high boiling materials and higher oligomers of lactic acid. The bottoms are withdrawn as bottoms stream 9. These can be discarded or recycled, with or without treatment, to an earlier step in the process.

The crude lactide produced in lactide reactor 2 contains mainly meso-, S,S- and R,R-lactide, water, lactic acid, and some linear lactic acid oligomers mainly having a degree of polymerization of up to about 6. Other impurities, including intermediate-boiling impurities may be present. The lactide concentration in the crude lactide is generally in excess of 80% by weight.

Crude lactide formed in lactide reactor 2 is withdrawn as stream 8 and, in the embodiment shown, is transferred to distillation column 3. Crude lactide stream usually is in the form of a vapor stream. In the embodiment shown, the crude lactide is distilled in three stages, in first distillation column 3, second distillation 4 and third distillation column 20, respectively. It is possible in principle at least to carry out this distillation in a single column or only two distillation columns. The three-stage distillation process illustrated in FIG. 1 has the advantages of simplifying the equipment that is needed in each stage, raising overall processing rates, and allowing conditions in each stage to be optimized for one or more specific separations that are to take place in that particular stage. It is particularly preferred to remove the more volatile impurities such as water and lactic acid from the lactide stream before separating the meso-lactide from the S,S- and R,R-lactide, especially when the meso-lactide is removed by fractional distillation as shown in FIG. 1.

Crude lactide stream 8 may be partially or fully condensed, if desired, before being sent onward to the separation step. In the embodiment shown, crude lactide stream 8 is introduced into first distillation column 3, where it is separated into partially purified crude lactide stream 10 and overhead stream 12. A bottoms stream (not illustrated) also may be withdrawn from first distillation column 3. Overhead stream 12 contains most of the water and lactic acid that were contained in crude lactide stream 8, together with a small portion of the lactide. The lactic acid portion of overhead stream 12 may include lactic acid that is carried over from lactide reactor 2, and may also include some lactic acid that is regenerated in first distillation column 3. Overhead stream 12 also contains other impurities and reaction by-products that are more volatile than meso-lactide, and may contain some amount of intermediate-boiling impurities. Overhead stream 12 may be discarded, but the lactic acid values at least are preferably recycled into an earlier step of the process, preferably directly or indirectly into step a) (as shown) or into the lactide reactor.

Partially purified crude lactide stream 10 contains S,S-lactide, R,R-lactide, meso-lactide, most of the intermediate-boiling impurities, and some high-boiling impurities such as linear lactic acid oligomers. It is normally substantially devoid of water and lower-boiling impurities.

In the embodiment shown, partially purified crude lactide stream 10 is transferred to second distillation column 4, where lactide is separated from higher-boiling impurities such as linear lactic acid oligomers. This produces purified crude lactide stream 21 and a bottoms stream 11. Purified crude lactide stream 21 contains intermediate-boiling impurities as described before, and may still contain some more volatile impurities. Some volatiles (mainly water and lactic acid) may in addition be removed from the second distillation column 4 via line 22. Bottoms stream 11 mainly includes high boiling materials and higher oligomers of lactic acid in a lactide matrix. It may be discarded or recycled to an earlier stage in the process; in the embodiment shown, bottoms stream 11 and volatiles removed via line 22 are both recycled via line 19 into lactide reactor 2 to recover lactic acid values from those streams.

Purified crude lactide stream 21 is then separated to remove meso-lactide and form a purified S,S- and R,R-lactide stream. In the embodiment shown in FIG. 1, purified crude lactide stream 21 is transferred to third distillation column 20, where meso-lactide is separated from S,S- and R,R-lactide. As shown, this produces a purified S,S-lactide/R,R-lactide stream 13, which is withdrawn from near or at the bottom of third distillation column 20; a meso-lactide stream 14, which is withdrawn from near or at the top of third distillation column 20, and an optional intermediate stream 15, which contains intermediate-boiling impurities and meso-lactide. In a commercial scale operation, it may be difficult to withdraw a significant intermediate stream 15 without also withdrawing a large amount of meso-lactide, and so taking such an intermediate stream may not be practical, and can be omitted. A bottoms stream (not shown) may also be removed from third distillation column 20.

Impurities that are introduced into third distillation column 20 with purified crude lactide stream 21 will partition between meso-lactide stream 14 and purified S,S- and R,R-lactide stream 13 (as well as intermediate stream 15 if such a stream is withdrawn). The highly volatile and intermediate-boiling impurities will become more concentrated in meso-lactide stream 14 if no intermediate stream 15 is taken. At least a portion of meso-lactide stream 14 is recycled back into steps a) and/or b) of the process, i.e., directly or indirectly into prepolymer reactor 1 and/or lactide reactor 2. In the particular embodiment shown in FIG. 1, meso-lactide stream 14 is recycled into lactide reactor 2 as stream 14A. Stream 14A is shown feeding directly into lactide reactor 2, but this stream can be combined with low molecular weight poly(lactic acid) stream 6, and the combined streams can be fed together into lactide reactor 2. Alternatively or in addition, meso-lactide stream 14 can be recycled into prepolymer reactor 1, directly as stream 14B or indirectly as stream 14C. In the embodiment shown, stream 14C is combined with lactic acid stream 5 and the combined streams are fed together into prepolymer reactor 1. Stream 14C and lactic acid stream 5 can be combined prior to, during, or after one or more upstream processes, such as evaporating the lactic acid solution to concentrate it.

At least a portion of the meso-lactide stream is recycled under conditions such that at least a portion of the meso-lactide in the recycled meso-lactide stream is converted to a mixture of S,S-, meso- and R,R-lactide. As the recycled meso-lactide stream contains mainly meso-lactide and only small quantities if any of S,S- or R,R-lactide, the recycled meso-lactide stream will be rich in both the S- and R-lactic acid values. It generally will contain at least 40% by weight of each type of lactic unit and more often 45% by weight of each type of lactic unit. The proportion of the non-predominant lactic unit (typically R-lactic units) in the recycled meso-lactide stream therefore is much higher than in the system as a whole. Therefore, the conversion of the recycled meso-lactide mixture will produce more of the non-predominant lactide to form than the system would produce without the meso-lactide recycle. In the more common case in which the S-enantiomer is predominant in the system, the "non-predominant lactide form" will be R,R-lactide. In that case, the meso-lactide recycle will increase the mole fraction of meso-lactide and R,R-lactide at the expense of a smaller mole fraction of S,S-lactide. In the rarer case in which the R-enantiomer is predominant in the system, the "non-predominant lactide form" will be S,S-lactide. There, more meso-lactide and S,S-lactide will be produced at the expense of R,R-lactide.

Meso-lactide conversion is favored under the conditions that generally prevail in steps a) and b) of the process, i.e., one or more of (1) elevated temperature, preferably from 100 to 300° C.; (2) the presence of hydroxyl-containing species, such as water, lactic acid, linear lactic acid oligomers and/or the low molecular weight poly(lactic acid) formed in step b); (3) the presence of a lactic acid polymerization/depolymerization catalyst and/or transesterification catalyst and (4) sufficient residence time under one or more of conditions (1), (2) and (3). It is preferred to provide from 0.2 to 10 equivalents of hydroxyl-containing species per kilogram of lactic units in steps a) and b). Conditions (1) and (2) generally exist in step a) of the process. Conditions (1), (2) and (3) generally exist in step b) of the process. Condition (4) generally exists in either step a) or step b), or in steps a) and b) combined. In a preferred process, one or both of steps a) and b) are conducted at a temperature of from 100 to 300° C., preferably from 150 to 250° C.; hydroxylic-containing species are present in step a) and step b); a lactic acid depolymerization catalyst is present in at least step b), and the residence time in either step a) or step b), or in steps a) and b) combined, is at least 15 minutes, preferably at least 30 minutes, more preferably at least 60 minutes. Residence times for purposes of this invention are determined as hold-up mass in a particular process step divided by the combined mass flow rates of all flow streams entering the process step. It is preferred to provide a residence time in step b) of at least 15 minutes, preferably at least 30 minutes. Residence times are generally not longer than necessary to convert the meso-lactide, in order to prevent undue amounts of racemization during steps a) and b).

Lactide can volatilize under the conditions of step b) at least, and often under the conditions of step a) as well. If the recycled meso-lactide simply volatilizes, little or none of it will convert to a mixture of S,S-, meso- and R,R-lactide. The point at which the meso-lactide is recycled and/or the manner in which it is recycled can be chosen to reduce or prevent the volatilization of the recycled meso-lactide.

It is generally preferred to condense the meso-lactide stream prior to recycling, if the meso-lactide stream is produced in the form of a vapor.

In some embodiments, the meso-lactide stream is recycled directly into step a) or indirectly (upstream) of step a), such as, for example, via lines 14B or 14C in FIG. 1. Conditions at those points in the process are generally not sufficient to volatilize a significant amount of the lactide, and so the recycled lactide can mix into the liquid phase that is present in those points in the process. Once mixed in, the meso-lactide does not become volatilized as rapidly when it is introduced into prepolymer reactor 1.

It is also possible to recycle the meso-lactide stream into step b) of the process, such as via line 14A in FIG. 1. Revolatilization of the recycled meso-lactide during step b) can be reduced or prevented by several methods, including for example, (1) introducing the meso-lactide stream into the step b) as a sub-cooled liquid, (2) pre-blending the meso-lactide stream with the low molecular weight poly(lactic acid) stream before introducing them into step b), (3) introducing the meso-lactide stream at or below the surface of the low molecular weight poly(lactic acid) in the step b), or (4) providing for a separate hydrolysis step of the meso-lactide stream, prior to recycling it. Combinations of two or more of these steps can be used, and other approaches may also be useful. A "sub-cooled" liquid is one which is at a temperature less than the temperature at which volatilization of that stream would occur at the pressure of the vessel in which step b) is performed.

Lactide molecules are believed to form primarily by the removal of two adjacent lactic units from one end of a linear poly(lactic acid) species. The conversion of meso lactide to a mixture of lactide forms is believed to depend on the meso-lactide becoming incorporated into such linear species in such a manner that a portion of the meso-lactide forms R,R- and S,S-dyads that come off together to form R,R- and S,S-lactide, respectively. The recycled meso-lactide engages in one or more oligomerization and/or transesterification reactions, after which lactide molecules re-form. The oligomerization and/or transesterification processes permit the S- and R-lactic units in the meso-lactide to become more randomly distributed, so that S,S-, meso- and R,R-lactide can all be created when lactide reforms. Direct racemization of meso-lactide may contribute to the production of the lactide mixture, but this is thought to play at most a very minor role.

Lactide can oligomerize through several mechanisms. The low molecular weight poly(lactic acid) formed in step b) of the process is hydroxyl- or carboxyl-terminated. Lactide can polymerize onto the hydroxyl end groups to extend the polymer chain, thereby increasing its molecular weight. Lactide also can hydrolyze when exposed to water, or ring-open and add to lactic acid or other low molecular weight hydroxyl-containing species that are present in the prepolymer and/or lactide reactors. It may also subsequently undergo a condensation reaction with the low molecular weight poly(lactic acid) present in step b) or react with more lactide. A ring-opened lactide molecule can engage in transesterification reactions with an existing low molecular weight poly(lactic acid) molecules that are present in steps a) and/or b) of the process.

Although the invention is not limited to any theory, the increase in the proportion of the less predominant lactide form due to meso-lactide recycle can be explained as follows (presuming for illustration purposes that the S-enantiomer is predominant in the system). R,R-lactide is created when two adjacent R-lactic units form in a low molecular weight poly (lactic acid) oligomer or polymer and are then removed together from the chain to form a lactide molecule. A single meso-lactide molecule, having one S- and one R-lactic unit, cannot by itself form two adjacent R-lactic units when it becomes incorporated into a poly(lactic acid) molecule. However, if a meso-lactide molecule adds in a head-to-head fashion onto the end of a poly(lactic acid) chain that is already terminated with an R-lactic unit, adjacent R-lactic units can be formed in the prepolymer as follows:

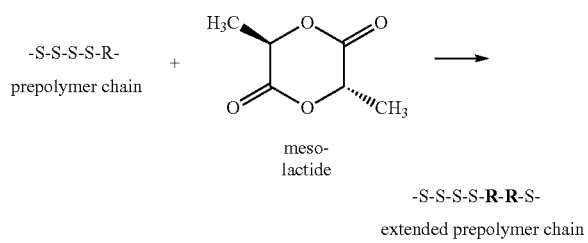

When the extended polymer chain shown in this reaction scheme depolymerizes, the highlighted adjacent R-lactic units will come off the polymer chain together some fraction of the time to produce R,R-lactide.

Adjacent R-lactic units can also be formed in a low molecular weight poly(lactic acid) when two lactide molecules add sequentially to a polymeric or oligomeric chain in a head-to-head fashion, as follows:

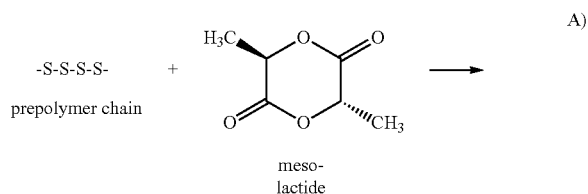

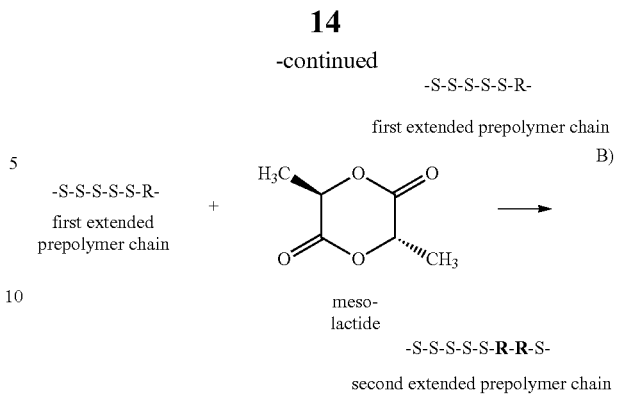

As before, the highlighted adjacent R-lactic units will come off the chain some fraction of the time to produce R,R-lactide.

A third way of producing adjacent R-lactic units in a low molecular weight poly(lactic acid) is through a transesterification reaction. This can occur, for example, between two polymer chains, as follows:

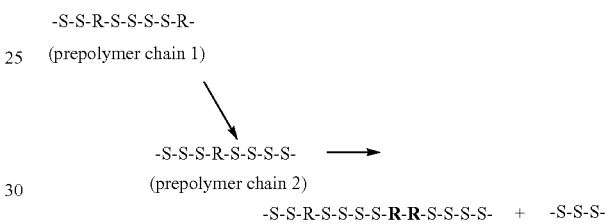

(transesterified prepolymers)

The highlighted adjacent R-lactic units in the transesterified polymer will once again come off the polymer chain together some fraction of the time to produce R,R-lactide.

Direct coupling of low molecular weight poly(lactic acid) molecules may also occur under the conditions in steps a) or b), and can contribute to the formation of chains with adjacent R-lactic units.

S,S-lactide can be produced in analogous ways.

The formation of adjacent R-lactic units (and adjacent S-lactic units) during any of the foregoing processes will be mainly statistically determined, provided enough reaction time is permitted to allow the recycled meso-lactide to assume a more or less random distribution. Assuming such a random distribution, the proportions of R,R-, S,S- and meso-lactide that are produced can be estimated as:

$$S,S\text{-lactide mole fraction} \approx (F_S)^2$$

$$R,R\text{-lactide mole fraction} \approx (F_R)^2$$

$$\text{Meso-lactide mole fraction} \approx 2F_R F_S$$

wherein $F_R$ is the mole fraction of R-lactic enantiomer and $F_S$ is the mole fraction of S-lactic enantiomer in step b) of the process. Therefore, when the proportion of the R-lactic units is increased (in a system in which the S-lactic form is predominant) by recycling meso-lactide, a larger mole fraction of R,R-lactide will be formed. The result of recycling the meso-lactide stream in such a system, therefore, is that the mole fraction of R,R-lactide is increased in the crude lactide stream leaving the lactide reactor. When R-lactic units predominate in the system, recycling meso-lactide will increase the mole fraction of S,S-lactide in the crude lactide.

Therefore, the effect of recycling the meso-lactide stream is that the mole fractions of meso-lactide and the non-predominant lactide form each will be increased in the crude lactide, at the expense of a lower mole fraction of the predominant lactide form. The mole fractions of each form of lactide that are produced in step b) of the process will mainly depend on (1) the relative sizes of the recycled meso-lactide stream and the concentrated lactic acid or lactic acid derivative stream that is fed into the prepolymerization step a), (2) the amount of racemization that occurs in the process up to the point of lactide formation, and (3) the optical purity of the initial feedstock. Some racemization of lactide may occur in downstream operations, but this is amount is usually very small and has little effect on the mole fractions of the various forms of lactide produced in the system.

Enough meso-lactide can be recycled in accordance in the invention to provide from 0.015 to 0.5 moles of lactic units in the meso-lactide recycle stream per mole of lactic units contributed by the lactic acid or lactic acid derivative that is used as a starting material in step a). Between these values, the amount of meso-lactide that is recycled will be selected to produce the desired mole fractions of S,S-, meso and R,R-lactide in the crude lactide, taking into account the optical purity of the starting lactic acid or derivative and the amount of racemization that occurs in the system. It is preferred to recycle enough meso-lactide to provide up to 0.25 moles of lactic units per mole of lactic unit contributed by the lactic acid or lactic acid derivative used as a starting material in step a), as larger recycle streams may be difficult or inefficient to handle. A preferred minimum amount of meso-lactide recycle is enough to provide at least 0.05 moles, more preferably at least 0.10 moles of lactic units per mole of lactic units contributed by the lactic acid or lactic acid derivative that is used as a starting material in step a).

In systems in which the amount of racemization is nearly constant over time (or is very small), and in which the optical purity of the initial feedstock is essentially constant, the amount of meso-lactide that is recycled can be used as a process control by which the mole fractions of S,S-, R,R- and meso-lactide in the crude lactide are managed. As more meso-lactide is recycled, the level of the non-predominant lactic units in the system will gradually increase and more of the non-predominant lactide form (either S,S- or R,R-lactide) will be produced and taken out in the S,S- and R,R-lactide stream. Conversely, recycling less meso-lactide will cause the level of less predominant lactic units in the system to drop, reducing the amount of the less predominant lactide form that is produced and removed with the S,S- and R,R-lactide stream.

So, for example, if a highly optically pure lactide stream is wanted, the meso-lactide recycle stream is reduced or stopped altogether, and, in response, a smaller mole fraction of the less predominant lactide form is produced. If a greater mole fraction of the non-predominant lactide is wanted, a greater amount of meso-lactide can be recycled.

In specific embodiments, the amount of the meso-lactide recycle stream is selected such that the mole fraction of the non-predominant lactide that is produced in step b) increases by 0.01 to 0.05, relative to the case wherein none of the meso-lactide stream is recycled. In addition, recycling of the meso-lactide stream in accordance with the invention can be performed to produce a crude lactide stream in step b) in which the mole fractions of the lactides are from 0.50 to 0.85 S,S-lactide, from 0.145 to 0.45 meso-lactide and from 0.005 to 0.05 R,R-lactide, or from 0.50 to 0.85 R,R-lactide, from 0.145 to 0.45 meso-lactide and from 0.005 to 0.05 S,S-lactide. More preferably, the recycling of the meso-lactide stream is performed to produce a crude lactide stream in which the mole fractions of the lactide are from 0.60 to 0.82 S,S-lactide, from 0.16 to 0.39 meso-lactide and from 0.01 to 0.04 R,R-lactide, or from 0.60 to 0.82 R,R-lactide, from 0.16 to 0.39 meso-lactide and from 0.01 to 0.04 S,S-lactide. More preferably, the mole fractions of lactides in the lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide.

The present process permits the composition of the purified S,S- and R,R-lactide stream that is produced in step c) of the process to be managed by controlling (1) the amount of meso-lactide that is recycled and (2) the amount of meso-lactide that is removed from the crude lactide.

S,S- and R,R-lactide usually will be removed together from step c) of the process, because they share melting and boiling temperatures, and are difficult to separate from each other unless a crystallization process is used As in previous processes, the meso-lactide can be more or less completely separated from the S,S- and R,R-lactide stream, as may be necessary in a particular case to produce lactide polymerization stream that is suitable for producing a specific grade of polylactide. In addition, meso-lactide that is separated from the S,S- and R,R-lactide stream can be stockpiled if necessary, and added into an S,S- and R,R-lactic stream as needed to produce a more amorphous grade of polylactide. Stockpiled meso-lactide also can be stored to be recycled through the process at some later time, when it is desired to produce more of the non-predominant lactide.

In this process, many impurities that are present in the meso-lactide stream (especially intermediate-boiling impurities) will be recycled with the meso-lactide, unless they are somehow removed from the meso-lactide stream before it is recycled.

There are several approaches for removing impurities from the meso-lactide stream. One approach is a distillation approach, an example of which is shown in FIG. 1, in which intermediate stream 15 is removed from third distillation column 20. Alternatively, meso-lactide stream 14 can be subjected to another distillation to separate it from all or a portion of the impurities. However, distillation approaches may be difficult to achieve economically because the intermediate-boiling impurities have boiling temperatures that are close to that of meso-lactide.

Another approach is to take a portion of the meso-lactide stream out of the system as a purge stream. In FIG. 1, this is illustrated as purge stream 16 which it taken from meso-lactide stream 14 and removed from the system. The purge stream will contain meso-lactide and impurities. The rate at which the purge stream is removed is generally selected such that the level of impurities in the system remains at or below some predetermined maximum amount. Thus, the size of the purge stream that is removed will depend on the rate at which impurities form in the system and the concentration of impurities in the meso-lactide stream. If the concentration of impurities reaches too high a level in the system, a larger purge stream can be removed to reduce that concentration. Generally, the purge stream will be discarded or used for low-value applications. Removal of such a purge stream has the effect of removing a disproportionate amount of the less predominant lactic units from the system. Therefore, taking a purge stream can be used as an additional means to control the build-up of the less predominant lactic units in the system.

A third approach to separating impurities from meso-lactide is an extraction and/or chemical treatment method. In the FIGURE, box 17 represents a unit operation for performing such an extraction or chemical treatment method. In general, methods of this type include (a) extraction with a solvent in which either the meso-lactide or the impurities (or some subset thereof), but not both, have a good solubility; (b) converting the meso-lactide and/or the impurities (or some subset thereof) to different chemical species which are more easily separated from each other, and then separating the impurities or their reaction products from the meso-lactide or its reaction products, as the case may be. In the latter case, the separation may be done by a further distillation, an extraction process, an adsorption process, a filtration process (if a solid chemical species is formed), or other separation technique, depending of course on the particular chemical species that are formed in a given case.

Still another method is to use melt or solvent crystallization methods to separate meso-lactide from the impurities.

Succinic anhydride is often a significant component of the intermediate-boiling impurities. Succinic anhydride can be separated from meso-lactide by washing the meso-lactide stream with a weakly basic aqueous phase. A suitable pH of the washing solution is in the range of from about 7.2 to about 11. This is believed to hydrolyze the succinic anhydride to form succinic acid. Some of the lactide may also be hydrolyzed to form mainly linear oligomers and possibly some lactic acid. The succinic acid is much more soluble in the basic aqueous phase than in the lactide phase, and will partition to the aqueous phase. The aqueous and organic phases are then separated to form a washed meso-lactide stream having a reduced level of succinic anhydride and perhaps other intermediate-boiling impurities. The washed meso-lactide stream can be recycled as described before.

An alternative extraction process relies on the relative speed of hydrolysis of the succinic anhydride, relative to lactide, to form the ring opened succinic acid in a predominantly lactide phase. This then can be extracted by an amine based extractant, or other extractants aimed at extracting organic acids, or by an adsorbent.

In yet another embodiment, the lactide can be more fully hydrolyzed to yield lactic acid and succinic acid, and the lactic acid can be recovered by distillation, leaving the succinic acid in the residue.

Alternatively, it is possible to recycle intermediate-boiling impurities with the meso-lactide stream. Intermediate-boiling impurities that are recycled in this manner can be removed from the system through various purge streams from the prepolymerization step, the lactide formation step or in the separation step or steps, including those indicated in FIG. 1 by lines 7, 9 and 11.

The purified S,S- and R,R-lactide stream that is removed from the system in most cases can be used as a monomer source for producing a polylactide. In FIG. 1, the purified S,S- and R,R-lactide stream is taken from third distillation column 20 via line 13. This stream is polymerized in polymerization unit 23 to produce polylactide stream 13A. The polymerized product is devolatilized to produce devolatilization stream 24. As shown, stream 24 is recycled into lactide reactor 2 via line 19, although stream 24 can instead be discarded or recycled elsewhere into the process.

No special polymerization methods are required. A particularly suitable process for preparing the polylactide resin is described in U.S. Pat. Nos. 5,247,059, 5,258,488 and 5,274,073. In the process described in those patents, lactide is fed as a liquid directly to a polymerization system, where it is polymerized at elevated temperature in the presence of a catalyst. As molecular weight increases, an equilibrium is established between the polymer and free lactide, thus limiting the build-up of molecular weight and producing a polymer containing a certain amount of free lactide. The free lactide provides some plasticizing effect that is often undesirable, and also tends to coat the surfaces of polymer processing equipment. For these reasons, the polymerization process typically includes a devolatilization step during which the free lactide content of the polymer is reduced, preferably to less than 1% by weight, and more preferably less than 0.3% by weight.

The polymerization can be conducted batch-wise, semi-continuously or continuously. Continuous stirred tank reactors (CSTRs) and tube or pipe reactors are suitable types of polymerization vessels. A series of CSTRs or tube or pipe reactors may be used to conduct the polymerization in stages. This permits additives to be introduced at specific stages in the polymerization process if desired, and also allows for different reaction conditions to be used at different stages of the polymerization.

Suitable polymerization temperatures preferably are (for solventless processes) above the melting temperature of the monomer or monomer mixture and above the melting temperature of the product copolymer, but below the temperature at which significant polymer degradation occurs. A preferred temperature range is from about 100° C. to about 220° C. A more preferred temperature range is from 120° C. to about 200° C. and especially from about 160° C. to about 200° C. Residence times at polymerization temperatures are selected to produce a polymer of the desired molecular weight and/or desired conversion of monomers. Molecular weight control agents, such as described in U.S. Pat. No. 6,277,951 can also be added to obtain the desired molecular weight.

Molecular weight and conversion are controlled by polymerization time and temperature, the equilibrium between free lactide and the polymer, and by the use of initiator compounds. In general, increasing quantities of initiator compounds on a molar basis will tend to decrease the molecular weight of the product polymer. The polymerization is conducted in the presence of a metal-containing catalyst. Examples of these catalysts include various tin compounds such as $SnCl_2$, $SnBr_2$, $SnCl_4$, $SnBr_4$, SnO, tin (II) bis(2-ethyl hexanoate), butyltin tris(2-ethyl hexanoate), hydrated monobutyltin oxide, dibutyltin dilaurate, tetraphenyltin and the like; PbO, zinc alkoxides, zinc stearate, compounds such as aluminum alkoxides, compounds such as antimony triacetate and antimony (2-ethyl hexanoate), compounds such as bismuth (2-ethyl hexanoate), calcium stearate, magnesium stearate, certain yttrium and rare earth compounds such as are described in U.S. Pat. No. 5,208,667 to McLain et al., and the like. Catalysts are used in catalytically effective amounts, which depend somewhat on the particular catalyst, but are usually in the range of from about 1 mole of catalyst to about 3000-50,000 moles of monomers. Preferred catalyst concentrations are not more than one mole of catalyst per 5000 moles of monomers, and especially not more than one mole of catalyst per 10,000 moles of monomers.

The resulting PLA resin contains metal catalyst residues, which are preferably deactivated by contacting the PLA resin with a deactivating agent.

In some cases, the S,S- and R,R-lactide stream (such as stream 13 in FIG. 1) will contain little or no meso-lactide. In such a case, all or nearly all of the non-predominant lactic units in the stream are present in the form of the corresponding non-predominant lactide form (either S,S-lactide or, more usually R,R-lactide). When such a stream is polymerized, the mole fraction of the non-predominant lactide in the stream will mainly control the ratio of S- to R-enantiomers in the polylactide.

However, it is within the scope of this invention to adjust the ratio of the S- and R-lactic units in the S,S- and R,R-lactide stream by operating the separation step such that some meso-lactide remains in the purified S, S- and R,R-lactide stream. One might do this, for example, in cases in which the S,S- and R,R-lactide stream does not contain enough of the less predominant lactide form to produce the desired grade of polylactide resin. In the usual case in which the S-lactic units predominate, leaving more meso-lactide will increase the proportion of R-lactic units in the stream, which will tend to produce a less crystalline grade of polylactide. The same effect can be achieved by mixing the S,S- and R,R-lactide stream with additional meso-lactide. It is also possible to adjust the enantiomer ratio in the stream by mixing it with additional S,S-lactide or R,R-lactide before it is polymerized.

Because the S,S- and R,R-lactide stream contains less meso-lactide than in conventional processes (at a given mole fraction of the less predominant enantiomeric lactic form) the polylactide produced from that stream will have somewhat different polymer structure than before. When this S,S-lactide/R,R-lactide mixture is polymerized, the non-predominant lactic units will tend form dyads in the polylactide product. When an S,S-lactide/meso-lactide mixture is polymerized instead, these dyads will rarely form in the polylactide product. Replacing meso-lactide with R,R-lactide therefore has the effect of increasing the average length of the segments of the less predominant lactic unit in the polylactide.

On the other hand, substituting the non-predominant lactide for meso-lactide on an equimolar basis has at most a small effect on the average length of the segments of the predominant enantiomer. In effect, substituting the less predominant lactide for meso-lactide, allows one to increase the proportion of the non-predominant lactic units in the polymer without significantly changing the length of the segments of the predominant lactic units. More generally, the length of the segments of the predominant lactic units becomes less sensitive to the proportion of the less predominant lactic units in the polylactide, when the less predominant lactide replaces meso-lactide in the polymerization mixture. The same effect is seen when S,S-lactide replaces meso-lactide in a system in which the R-enantiomer is predominant.

The average lengths of sequences of S- and R-lactic units in a polylactide can be determined using NMR methods as described, for example, by K. Thakur et al. in "A Quantitative Method for Determination of Lactide composition in Poly (lactide) Using 1H NMR", Anal. Chem. 1997, 69, 4303-4309.

The crystalline properties of a semi-crystalline polylactide depend very little on the length of the segments of the less predominant enantiomer (again, typically R-lactic units), but those properties depend quite significantly upon the length of the segments of the predominant enantiomer (typically S-lactic units). This tendency holds when one enantiomer is predominant enough that the polymer is semi-crystalline. This corresponds to an enantiomer ratio of approximately 85:15 or greater, preferably 92:8 or greater. A higher content of the less predominant lactic units can be tolerated to achieve a given set of crystalline properties. In addition, polymer properties are less sensitive to enantiomer ratios. Therefore, a greater variation in the content of the less predominant lactic units can be tolerated in an S,S-lactide/R,R-lactide copolymer. The mole fractions of S- and R-lactic units do not have to be controlled as stringently in the process.

Crystalline properties of a polylactide can be expressed in terms of the crystallization melting temperature of the resin, and also in terms of the crystallization half-time, which is a measure of the rate of crystallization. Crystalline melting temperatures can be measured by differential scanning calorimetry (DSC) as follows. A sample is heated to 250° C. and held at that temperature long enough to melt out all crystallites. The sample is then cooled to ~110-130° C. at 50° C./minute or faster and then held at ~110-130° C. to allow crystallites to form. It is then heated at 50° C./minute and the crystalline melting temperature(s) determined. Crystalline melting temperature is defined as the temperature of the endothermic peak center under melt-out.

"Crystallization half-time" is determined by DSC, and provides an indication of crystallization rates for a polylactide resin. It can be evaluated as follows: a sample is melted at 250° C. for a period long enough to melt out all crystallinity, and then cooled at 50° C./minute or faster to 130° C. The sample is held at 130° C. and allowed to crystallize at that temperature until no further crystals develop. The enthalpy of crystallization is tracked as a function of time. The time required to develop one-half of the final crystallinity is the crystallization half-time. The sample is then heated at 250° C. to melt out the crystallites and so determine the melting temperature of the crystallites that have formed. It has been found that polylactides in which the less predominant lactic units are contributed mainly from non-predominant lactide will in most cases have a crystallization half-time that is equal to or shorter than that of a similar polylactide, having an equivalent content of the less predominant lactic units, in which the less predominant lactic units are contributed mainly from meso-lactide. In many cases, crystallization half-times equivalent to those of conventional polylactide resins can be obtained, even at a higher level of the less predominant enantiomer. Therefore, a higher proportion of the less predominant enantiomer can be present in an S,S-lactide/R,R-lactide copolymer than in an S,S-lactide/meso-lactide or R,R-lactide/meso-lactide copolymer, while retaining equivalent crystallization rates.

In one embodiment of the invention, the mole fractions of lactides in the purified S,S- and R,R-lactide stream obtained in step c) in the process are at least 0.80 S,S-lactide, from 0.005 to 0.20 R,R-lactide and from 0 to 0.10 meso-lactide, and the mole fraction of meso-lactide is less than or equal that of R,R-lactide. In another embodiment, those mole fractions are at least 0.90 S,S-lactide, from 0.005 to 0.10 R,R-lactide and from 0 to 0.05 meso-lactide, and the mole fraction of meso-lactide is less than or equal that of R,R-lactide. In another embodiment, those mole fractions are at least 0.95 S,S-lactide, from 0.005 to 0.05 R,R-lactide and from 0 to 0.025 meso-lactide, and the mole fraction of meso-lactide is less than or equal that of R,R-lactide. In any of these embodiments, the mole fraction of meso-lactide in the purified S,S- and R,R-lactide stream may be is from 0 to 0.05, from 0 to 0.03 or from 0 to 0.01. The respective mole fractions are controlled in the inventive process primarily through the amount of meso-lactide that is recycled, and the extent to which meso-lactide is removed from the crude lactide in step c) of the process.

In other embodiments, in which the R-enantiomer is predominant in the system, the mole fractions of lactides contained in the purified S,S- and R,R-lactide stream produced in step c) are at least 0.80 R,R-lactide, from 0.005 to 0.20 S,S-lactide and from 0 to 0.10 meso-lactide, and the mole fraction of meso-lactide is less than or equal that of S,S-lactide. Those mole fractions may be at least 0.90 R,R-lactide, from 0.005 to 0.10 S,S-lactide and from 0 to 0.05 meso-lactide, and the mole fraction of meso-lactide is less than or equal that of S,S-lactide, or they may be at least 0.95 S,S-lactide, from 0.005 to 0.05 R,R-lactide and from 0 to 0.025 meso-lactide. In any of these embodiments, the mole fraction of meso-lactide in the purified S,S- and R,R-lactide stream may be is from 0 to 0.05, from 0 to 0.03 or from 0 to 0.01. As before, the respective mole fractions are controlled in the inventive process primarily through the amount of meso-lactide that is recycled, and the extent to which meso-lactide is removed from the crude lactide in step c) of the process.

The process of the invention facilitates the production of various polylactide copolymers which are new and have beneficial crystallization properties. These new copolymers can be described generally as copolymers of a lactide mixture containing S,S-lactide, R,R-lactide and optionally meso-lactide, wherein a) either the S,S-lactide or R,R-lactide is predominant in the lactide mixture and the other is non-predominant, and b) the lactide mixture contains at least 80% of the predominant lactide, 0.5 to 20% of the non-predominant lactide, and from 0 to 10% of meso-lactide, all based on the weight of lactides in the mixture and c) the amount of meso-lactide that is present is less than or equal to the amount of the non-predominant lactide.

A specific copolymer is of a lactide mixture containing S,S-lactide, R,R-lactide and optionally meso-lactide, wherein a) either the S,S-lactide or R,R-lactide is predominant in the lactide mixture and the other is non-predominant, b) the lactide mixture contains at least 88 to 99.5% of the predominant lactide, from 0.5 to 12% of the non-predominant lactide, and either no meso-lactide or an amount of meso-lactide that is less than or equal to the amount of the non-predominant lactide.

Another specific preferred copolymer is of a lactide mixture containing S,S-lactide, R,R-lactide and optionally meso-lactide, wherein a) either the S,S-lactide or R,R-lactide is predominant in the lactide mixture and the other is non-predominant, b) the lactide mixture contains from 90 to 99.5% of the predominant lactide, from 0.5 to 10% of the non-predominant lactide, and either no meso-lactide or an amount of meso-lactide that is less than or equal to the amount of the non-predominant lactide.

Still another specific copolymer is of a lactide mixture containing S,S-lactide, R,R-lactide and optionally meso-lactide, wherein a) either the S,S-lactide or R,R-lactide is predominant in the lactide mixture and the other is non-predominant, b) the lactide mixture contains from 92 to 99.5% of the predominant lactide, from 0.5 to 8% of the non-predominant lactide, and either no meso-lactide or an amount of meso-lactide that is less than or equal to the amount of the non-predominant lactide.

A preferred copolymer is of a lactide mixture containing S,S-lactide, R,R-lactide and optionally meso-lactide, wherein a) either the S,S-lactide or R,R-lactide is predominant in the lactide mixture and the other is non-predominant, b) the lactide mixture contains from 95 to 99.5% of the predominant lactide, from 0.5 to 5% of the non-predominant lactide, and either no meso-lactide or an amount of meso-lactide that is less than or equal to the amount of the non-predominant lactide.

A preferred copolymer is of a lactide mixture containing S,S-lactide, R,R-lactide and optionally meso-lactide, wherein a) either the S,S-lactide or R,R-lactide is predominant in the lactide mixture and the other is non-predominant, b) the lactide mixture contains 97-99.5% of the predominant lactide, 0.5 to 3% of the non-predominant lactide, and either no meso-lactide or an amount of meso-lactide that is less than or equal to the amount of the non-predominant lactide.

In each of these specific copolymers, the amount of meso-lactide can be no more than one-half, no more than one-quarter, or no more than one-tenth the amount of the non-predominant lactide. The non-predominant lactide will be R,R-lactide in most cases, but can be S,S-lactide, in each of these specific copolymers.

The following example is provided to illustrate the invention, but not to limit the scope thereof. All parts and percentages are by weight unless otherwise indicated.

EXAMPLE 1 AND 2 AND COMPARATIVE RUNS A AND B

A lactide/polylactide manufacturing system as schematically diagrammed in FIG. 1 is operated. A fresh stream of a 64% lactic acid solution in water is fed into prepolymer reactor 1 through line 5. The lactic acid in this stream is 99.8% S-lactic acid and 0.2% R-lactic acid. An overhead stream is taken from prepolymer reactor 1 through line 7. Prepolymer is transferred through line 6 to lactide reactor 2, with addition of catalyst through line 18. A purge stream is taken from lactide reactor 2 through line 9. Crude lactide is taken via line 8 to first distillation column 3. An overhead stream, which contains most of the water and lactic acid contained in the crude lactide, together with a small amount of lactide and some linear lactic acid oligomers, is taken from first distillation column 3 through line 12; the contents of that stream are combined with the fresh lactic acid stream entering prepolymer reactor 1 through line 5, and recycled in that manner. Partially purified crude lactide is transferred to second distillation column 4 through line 10. An overhead stream is taken from second distillation column 4 through line 22, and a bottoms stream is taken through line 11. The overhead stream contains mainly water, lactic acid or linear lactic acid oligomers, and some lactide.

A purified crude lactide steam is transferred to third distillation column 20 via line 21, where meso-lactide is separated from S,S- and R,R-lactide. A product stream is taken from third distillation column 20 via line 13. The separation is made so that the R-enantiomer content of product stream 13 is 1.5%. This product stream is polymerized in polymerization unit 23 to produce polylactide stream 13A. The polymerized product is devolatilized to produce devolatilization stream 24. Stream 24 is combined with streams 11 and 22, and they are recycled together into lactide reactor 2 via line 19.

A meso-lactide stream is taken from third distillation column 20 via line 14. No intermediate-boiling impurities stream 15 or purge stream 16 is taken.

Conditions in the prepolymer reactor are: pressure of about 80 mm Hg; temperature of 170° C. and average residence time of about 3 hours. Conditions in the lactide reactor are 220° C., 10-15 mm Hg pressure, 1500 ppm tin catalyst, residence time 30-60 minutes.

In Comparative Run A, the meso-lactide stream is removed from the system and discarded. Flows through the system in this case are as follows:

Comparative Run A Mass Flows

| Line | Description | Mass/hr | % R |
|---|---|---|---|
| 5 | Fresh lactic acid feed | 25.2 (dry weight lactic acid) | 0.2 |
| 6 | Prepolymer | 29.3 | 3.4 |
| 7 | Prepolymer reactor overheads | 22 | N/A |
| 8 | Crude lactide | 41.0 | 9.9 |
| 9 | Lactide reactor bottoms | 1.2 | 9.9 |
| 10 | Partially purified lactide | 36.9 | 8.5 |

-continued

| Line | Description | Mass/hr | % R |
|---|---|---|---|
| 11 | Second distillation column bottoms | 8.0 | 6.9 |
| 12 | First distillation column overheads | 4.1 | 23.0 |
| 13 | Lactide product stream | 24.2 | 1.5 |
| 14 | Meso-lactide stream | 2.2 | 45.0 |
| 14A | Recycled meso-lactide stream | 0 | N/A |
| 15 | Intermediate-boiling impurities stream | 0 | 0 |
| 19 | Recycle stream | 12.9 | 8.4 |
| 21 | Purified lactide stream | 26.4 | 6.9 |
| 22 | Second distillation column overheads | 2.5 | 18.6 |
| 24 | Devolatilizer stream | 2.4 | 0.15 |

In Example 1, 0.45 mass units/hour of the meso-lactide stream 14 are recycled into lactide reactor 2 via line 14A, such that the lactide becomes reincorporated into the prepolymer. The conditions in the lactide reactor are sufficient to obtain a nearly random distribution of the recycled meso-lactide in the prepolymer. This increases the amount of R-enantiomer in the prepolymer which in turn increases the mole fractions of meso-lactide and R,R-lactide in the crude lactide stream. Flows in this case are as follows:

EXAMPLE 1 FLOWS

| Line | Description | Mass/hr | % R |
|---|---|---|---|
| 5 | Fresh lactic acid feed | 25.2 (dry weight lactic acid) | 0.2 |
| 6 | Prepolymer | 29.8 | 4.1 |
| 7 | Prepolymer reactor overheads | 22.0 | N/A |
| 8 | Crude lactide | 41.5 | 10.5 |
| 9 | Lactide reactor bottoms | 1.2 | 10.5 |
| 10 | Partially purified lactide | 37.4 | 8.5 |
| 11 | Second distillation column bottoms | 8.0 | 7.5 |
| 12 | First distillation column overheads | 4.2 | 23.0 |
| 13 | Lactide product stream | 24.4 | 1.5 |
| 14 | Meso-lactide stream | 2.5 | 45.0 |
| 14A | Recycled meso-lactide stream | 0.45 | 45.0 |
| 15 | Intermediate-boiling impurities stream | 0 | 0 |
| 19 | Recycle stream | 12.9 | 8.6 |
| 21 | Purified lactide stream | 26.9 | 7.5 |
| 22 | Second distillation column overheads | 2.5 | 19.2 |
| 24 | Devolatilizer stream | 2.4 | 0.15 |

In each of Comparative Run A and Example 1, the lactide product stream which is taken to polymerization contains 1.5% of R-lactic units. However, the composition of the lactide product stream is different in the two cases, as follows:

| | % S,S-lactide | % R,R-lactide | % Meso-lactide |
|---|---|---|---|
| Comparative Run A | 98.3 | 1.3 | 0.4 |
| Example 1 | 98.5 | 1.5 | 0.0 |

Yield to polymer is slightly higher in Example 1 (21.9/25.2=86.9%) than in Comparative Run A (21.8/25.2=86.5%).

In comparative Run A, 4.4% of the meso-lactide produced remains in the lactide product stream 13, whereas in Example 1, essentially none of the meso-lactide that is produced exits the system with product lactide stream 13. Because the meso-lactide is more completely separated in Example 1, the product lactide stream in that case contains fewer intermediate-boiling impurities than in Comparative Run A. In Comparative Run A, the intermediate-boiling impurities removed with meso-lactide stream 14 are purged from the system because that stream is discarded. In the Example 1 case, those impurities are recycled with the meso-lactide stream. Their accumulation in the system can be prevented by adjusting the volumes of purge streams such as streams 7, 9 and 16.

Note that in Example 1, the amount of meso-lactide that is recycled is smaller than the meso-lactide stream that is taken from third distillation column 20. The recycle stream in this case constitutes about 20% of the mass of the meso-lactide stream, meaning losses from the meso-lactide stream are reduced by at least that amount.

For Comparative Run B and Example 2, the fractional distillation column is operated to provide an S,S- and R,R-lactide product stream (13) that contains 4.0% of the R-enantiomer. In Comparative Run B, there is no meso-lactide recycle. In Example 2, 5.5 mass units/hour of meso-lactide is recycled into lactide reactor 2 via line 14A. Flows for these cases are as follows:

EXAMPLE 2 AND COMPARATIVE RUN B FLOWS

| | | Comparative Run B | | Example 2 | |
|---|---|---|---|---|---|
| Line | Description | Mass/hr | % R | Mass/hr | % R |
| 5 | Fresh lactic acid feed | 25.2 | 0.2 | 25.2 | 0.2 |
| 6 | Prepolymer | 29.3 | 3.4 | 35.4 | 10.2 |
| 7 | Prepolymer reactor overheads | 22.0 | N/A | 22.0 | N/A |
| 8 | Crude lactide | 41.2 | 10.1 | 47.5 | 16.5 |
| 9 | Lactide reactor bottoms | 1.2 | 10.1 | 1.2 | 16.5 |
| 10 | Partially purified lactide | 37.1 | 8.7 | 47.8 | 15.8 |
| 11 | Second distillation column bottoms | 8.0 | 7.1 | 8 | 13.6 |
| 12 | First distillation column overheads | 4.1 | 23.0 | 4.8 | 23.0 |
| 13 | Lactide product stream | 25.7 | 4.0 | 27.8 | 4.0 |
| 14 | Meso-lactide stream | 0.8 | 45.0 | 4.5 | 45.0 |
| 14A | Recycled meso-lactide stream | 0 | N/A | 5.5 | 45.0 |
| 15 | Intermediate-boiling impurities stream | 0 | N/A | 0 | N/A |
| 19 | Recycle stream | 13.1 | 8.7 | 13.3 | 13.1 |
| 21 | Purified lactide stream | 26.6 | 7.1 | 32.3 | 13.6 |
| 22 | Second distillation column overheads | 2.5 | 18.7 | 2.5 | 25.8 |
| 24 | Devolatilizer stream | 2.6 | 4.0 | 2.8 | 4.0 |

The composition of the lactide product stream from Example 2 is different than that of Comparative Run B, even though the R-enantiomer mole fractions are the same, as follows:

| | % S,S-lactide | % R,R-lactide | % Meso-lactide |
|---|---|---|---|
| Comparative Run B | 93.3 | 1.3 | 5.4 |
| Example 2 | 95.7 | 3.8 | 0.5 |

Yield to polymer is much higher in Example 2 (25.0/25.2 = 99.2%) than in Comparative Run B (23.2/25.2 = 92.1%).

In Comparative Run B, 65% of the total amount of meso-lactide produced remains in the lactide product stream 13, whereas in Example 2, only about 3% of the meso-lactide that is produced exits the system with product lactide stream 13. For that reason, the product lactide stream in Example 2 contains fewer intermediate-boiling impurities than in Comparative Run A. As with Example 1, the accumulation of intermediate-boiling impurities can be prevented in the Example 1 case by adjusting the volumes of purge streams such as streams 7, 9 and 16.

In Example 2, the amount of meso-lactide that is recycled is larger than the meso-lactide stream that is taken from third distillation column 20. This means that to continue steady-state operation, meso-lactide stream 14 needs to be supplemented with additional meso-lactide. This problem is easily solved whenever the plant produces multiple grades of polylactide resin. As shown in Example 1, the production of some grades of polylactide resin will produce an excess of meso-lactide above that amount which can be recycled when that grade is produced. The excess meso-lactide that is produced under the Example 1 conditions (or other conditions which produce an excess of meso-lactide) can be stockpiled and used in the Example 2 case to supplement the meso-lactide recycle. It is also possible to stop the recycle stream altogether in some cases to stockpile meso-lactide. An important advantage of the invention is that excess meso-lactide that is produced when a highly crystalline polylactide is made can still be used in high-value polylactide applications, by stockpiling the excess meso-lactide and using it when somewhat lower crystallinity grades of polylactide are produced.

EXAMPLE 3 AND COMPARATIVE RUN C

Lactic acid, with a nominal composition of 65 wt % lactic acid in water and consisting of >99% of the S-isomer, is processed to form a polymer grade lactide using a apparatus as generally described in the FIGURE. Conditions are generally as described in prior examples. Distillation column 20 is operated in each case to produce a product lactide stream containing about 4% of R-lactic units and 96% of S-lactic units. In Comparative Run C, no recycle of the meso-lactide stream is performed. In Example 3, meso-lactide is recycled to the lactide reactor (step b) of the process) via line 14A. Typical once-through process values (in mass units/hour) are indicated in Table 3. The effect on the meso-recycle on the enantiomeric composition of the product lactide stream (stream 13) that is taken for polymerization is also shown in Table 3, together with succinic acid levels in that stream.

TABLE 3

|  | Comp. Run C | Example 3 |
|---|---|---|
| Stream 5 | 40.2 | 38.8 |
| Stream 9 | 1.5 | 1.2 |
| Stream 13 | 20.6 | 19.3 |
| Stream 14 | 1.01 | 4.43 |
| Stream 14A | 0 | 2.45 |
| Stream 6 | 6.5 | 6.2 |
| Lactide reactor, % R | 10.2% | 15.3% |
| Stream 13, % R | 4.0% | 3.9% |
| Stream 13, % RR | 1.5% | 3.7% |
| Stream 13, % meso | 5.1% | 0.4% |
| Stream 13, succinic acid (ppm) | 1,280 | 480 |

As before, recycling meso-lactide, shifts the mole fractions of lactides towards higher R,R-lactide production. In Example 3, almost all of the R-lactic units in stream 13 are contributed by R,R-lactide, whereas in Comparative Run C, meso-lactide provides the bulk of the R-lactic units in that stream. Because meso-lactide is more cleanly separated from the S,S- and R,R-lactide in Example 3, succinic acid (a key intermediate-boiling impurity) levels are reduced significantly compared to the case of Comparative Run C.

What is claimed is:

1. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b),
   whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed,
   wherein during step b), the recycled meso-lactide stream is subjected to a temperature of from 180 to 250° C., hydroxylic species and a lactic acid polymerization/depolymerization catalyst are present, and the residence time in step b) is at least 15 minutes.

2. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b),
   whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed,
   wherein the meso-lactide stream is recycled into step a) or upstream of step a), and the recycled meso-lactide becomes mixed into a liquid phase that is present in the step a).

3. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b), whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed, wherein the meso-lactide stream is recycled into step b), and the meso-lactide stream is recycled by (1) introducing the meso-lactide stream into step b) as a sub-cooled liquid, (2) pre-blending the meso-lactide stream with the low molecular weight poly(lactic acid) formed in step a) and introducing them together into step b), (3) introducing the meso-lactide stream at or below the surface of the low molecular weight poly (lactic acid) in step b), (4) providing for a separate hydrolysis step of the meso-lactide stream prior to recycling the meso-lactide stream into step b) or (5) a combination of any two or more thereof.

4. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b),
   whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed,
   wherein the low molecular weight poly(lactic acid) is formed in step a) by polymerizing lactic acid or a lactic acid derivative, wherein the lactic acid or lactic acid derivative contains at least 90% of either the S- or R-enantiomer, and no more than 10% of the other enantiomer and further wherein enough of the meso-lactide stream is recycled to provide from 0.015 to 0.5 moles of lactic units per mole of lactic units contributed by the lactic acid or lactic acid derivative that is polymerized in step a).

5. The process of claim 4 wherein the lactic acid or lactic acid derivative contains at least 99% of either the S- or R-enantiomer, and no more than 1% of the other enantiomer.

6. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b),
   whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed,
   wherein the mole fraction of the non-predominant lactide in the crude lactide produced in step b) is increased by 0.01 to 0.05 relative to when step d) is not performed.

7. The process of claim 3 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide.

8. The process of claim 7 wherein the mole fractions of lactides contained in the purified S,S- and R,R-lactide stream produced in step c) are at least 0.95 S,S-lactide, from 0.005 to 0.05 R,R-lactide and from 0 to 0.025 meso-lactide, and the mole fraction of meso-lactide is less than or equal that of R,R-lactide.

9. The process of claim 8 wherein the mole fraction of meso-lactide in the purified S,S- and R,R-lactide stream is from 0 to 0.01.

10. The process of claim 7 wherein the mole fractions of lactides contained in the purified S,S- and R,R-lactide stream produced in step c) are at least 0.95 R,R-lactide, from 0.005 to 0.05 S,S-lactide and from 0 to 0.025 meso-lactide, and the mole fraction of meso-lactide is less than or equal that of S,S-lactide.

11. The process of claim 10 wherein the mole fraction of meso-lactide in the purified S,S- and R,R-lactide stream is from 0 to 0.01.

12. A process for producing a polymerizable lactide stream, comprising:
   a) forming a low molecular weight poly(lactic acid);
   b) depolymerizing the low molecular weight poly(lactic acid) to form a crude lactide that includes meso-lactide, S,S-lactide and R,R-lactide, wherein either S,S-lactide or R,R-lactide is the non-predominant lactide;
   c) separating meso-lactide from the crude lactide in one or more steps such that
      1) a meso-lactide-enriched stream is formed in which the mole fraction of meso-lactide is at least 0.8; and
      2) a purified S,S- and R,R-lactide stream is formed; and
   d) recycling at least a portion of the meso-lactide stream directly or indirectly back into step a) or step b),
   whereby at least a portion of the meso-lactide in the recycled meso-lactide stream is converted to a mixture of S,S-, meso- and R,R-lactide and the mole fraction of the non-predominant lactide in the crude lactide produced in step b) is increased relative to when step d) is not performed,
   wherein in step c), intermediate boiling impurities become concentrated in the meso-lactide-enriched stream and further wherein the meso-lactide-enriched stream contains succinic anhydride, and succinic anhydride is separated from the meso-lactide before step d).

13. The process of claim 3, further comprising polymerizing the purified S,S- and R,R-lactide stream produced in step c).

14. The process of claim 3, wherein step c) includes a melt crystallization step.

15. The process of claim 4, wherein step c) includes a melt crystallization step.

16. The process of claim 4 wherein the low molecular weight poly(lactic acid) is formed in step a) by polymerizing lactic acid or a lactic acid derivative, wherein the lactic acid or lactic acid derivative contains at least 90% of either the S- or R-enantiomer, and no more than 10% of the other enantiomer.

17. The process of claim 15 wherein enough of the meso-lactide stream is recycled to provide from 0.015 to 0.5 moles of lactic units per mole of lactic units contributed by the lactic acid or lactic acid derivative that is polymerized in step a).

18. The process of claim 17 wherein the lactic acid or lactic acid derivative contains at least 99% of either the S- or R-enantiomer, and no more than 1% of the other enantiomer.

19. The process of claim 4 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 S,S-lactide, from 0.005 to 0.05 R,R-lactide and from 0 to 0.025 meso-lactide, and the mole fraction of meso-lactide is less than or equal that of R,R-lactide.

20. The process of claim 19 wherein the mole fraction of meso-lactide in the purified S,S- and R,R-lactide stream is from 0 to 0.01.

21. The process of claim 4 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 R,R-lactide, from 0.005 to 0.05 S,S-lactide and from 0 to 0.025 meso-lactide, and the mole fraction of meso-lactide is less than or equal that of S,S-lactide.

22. The process of claim 21 wherein the mole fraction of meso-lactide in the purified S,S- and R,R-lactide stream is from 0 to 0.01.

23. The process of claim 4, further comprising polymerizing the purified S,S- and R,R-lactide stream produced in step c).

24. The process of claim 5, wherein step c) includes a melt crystallization step.

25. The process of claim 5 wherein the low molecular weight poly(lactic acid) is formed in step a) by polymerizing lactic acid or a lactic acid derivative, wherein the lactic acid or lactic acid derivative contains at least 90% of either the S- or R-enantiomer, and no more than 10% of the other enantiomer.

26. The process of claim 25 wherein enough of the meso-lactide stream is recycled to provide from 0.015 to 0.5 moles of lactic units per mole of lactic units contributed by the lactic acid or lactic acid derivative that is polymerized in step a).

27. The process of claim 26 wherein the lactic acid or lactic acid derivative contains at least 99% of either the S- or R-enantiomer, and no more than 1% of the other enantiomer.

28. The process of claim 5 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 S,S-lactide, from 0.005 to 0.05 R,R-lactide and from 0 to 0.025 meso-lactide, and the mole fraction of meso-lactide is less than or equal that of R,R-lactide.

29. The process of claim 28 wherein the mole fraction of meso-lactide in the purified S,S- and R,R-lactide stream is from 0 to 0.01.

30. The process of claim 5 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 R,R-lactide, from 0.005 to 0.05 S,S-lactide and from 0 to 0.025 meso-lactide, and the mole fraction of meso-lactide is less than or equal that of S,S-lactide.

31. The process of claim 30 wherein the mole fraction of meso-lactide in the purified S,S- and R,R-lactide stream is from 0 to 0.01.

32. The process of claim 5, further comprising polymerizing the purified S,S- and R,R-lactide stream produced in step c).

33. The process of claim 6, wherein step c) includes a melt crystallization step.

34. The process of claim 6 wherein the low molecular weight poly(lactic acid) is formed in step a) by polymerizing lactic acid or a lactic acid derivative, wherein the lactic acid or lactic acid derivative contains at least 90% of either the S- or R-enantiomer, and no more than 10% of the other enantiomer.

35. The process of claim 34 wherein enough of the meso-lactide stream is recycled to provide from 0.015 to 0.5 moles of lactic units per mole of lactic units contributed by the lactic acid or lactic acid derivative that is polymerized in step a).

36. The process of claim 35 wherein the lactic acid or lactic acid derivative contains at least 99% of either the S- or R-enantiomer, and no more than 1% of the other enantiomer.

37. The process of claim 6 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 S,S-lactide, from 0.005 to 0.05 R,R-lactide and from 0 to 0.025 meso-lactide, and the mole fraction of meso-lactide is less than or equal that of R,R-lactide.

38. The process of claim 37 wherein the mole fraction of meso-lactide in the purified S,S- and R,R-lactide stream is from 0 to 0.01.

39. The process of claim 6 wherein the mole fractions of lactides contained in the crude lactide produced in step b) are from 0.67 to 0.80 S,S-lactide, from 0.19 to 0.30 meso-lactide and from 0.01 to 0.03 R,R-lactide, or from 0.67 to 0.80 R,R-lactide, from 0.19 to 0.30 meso-lactide and from 0.01 to 0.03 S,S-lactide and the mole fractions of lactides contained in the purified S,S- and R,R-lactide stream produced in step c) are at least 0.95 R,R-lactide, from 0.005 to 0.05 S,S-lactide and from 0 to 0.025 meso-lactide, and the mole fraction of meso-lactide is less than or equal that of S,S-lactide.

40. The process of claim 39 wherein the mole fraction of meso-lactide in the purified S,S- and R,R-lactide stream is from 0 to 0.01.

41. The process of claim 6, further comprising polymerizing the purified S,S- and R,R-lactide stream produced in step c).

* * * * *